(12) United States Patent
Touitou

(10) Patent No.: US 11,590,230 B2
(45) Date of Patent: Feb. 28, 2023

(54) COMPOSITIONS OF THERAPEUTIC SUBSTANCES, METHODS AND USES THEREOF

(71) Applicant: Yissum Research Development Company of the Hebrew University of Jerusalem Ltd., Jerusalem (IL)

(72) Inventor: Elka Touitou, Hod Hasharon (IL)

(73) Assignee: Elka Touitou, Zichron Yaacov (IL)

( * ) Notice: Subject to any disclaimer, the term of this patent is extended or adjusted under 35 U.S.C. 154(b) by 0 days.

(21) Appl. No.: 15/781,639

(22) PCT Filed: Dec. 6, 2016

(86) PCT No.: PCT/IL2016/051303
§ 371 (c)(1),
(2) Date: Jun. 5, 2018

(87) PCT Pub. No.: WO2017/098502
PCT Pub. Date: Jun. 15, 2017

(65) Prior Publication Data
US 2019/0054176 A1    Feb. 21, 2019

Related U.S. Application Data

(60) Provisional application No. 62/263,868, filed on Dec. 7, 2015.

(51) Int. Cl.
| | | |
|---|---|---|
| *A61K 47/24* | (2006.01) |
| *A61K 9/06* | (2006.01) |
| *A61K 9/48* | (2006.01) |
| *A61K 31/352* | (2006.01) |
| *A61K 9/127* | (2006.01) |
| *A61P 29/02* | (2006.01) |
| *A61K 9/00* | (2006.01) |
| *A61K 31/05* | (2006.01) |

(52) U.S. Cl.
CPC ............ *A61K 47/24* (2013.01); *A61K 9/0053* (2013.01); *A61K 9/06* (2013.01); *A61K 9/127* (2013.01); *A61K 9/4858* (2013.01); *A61K 31/05* (2013.01); *A61K 31/352* (2013.01); *A61P 29/02* (2018.01)

(58) Field of Classification Search
CPC ........ A61K 47/24; A61K 31/352; A61K 9/06; A61K 9/0053; A61P 29/02
See application file for complete search history.

(56) References Cited

U.S. PATENT DOCUMENTS

| | | |
|---|---|---|
| 7,423,004 B2 | 9/2008 | Patel et al. |
| 2006/0160888 A1* | 7/2006 | Kottayil ............... A61K 9/4875 514/454 |
| 2012/0231083 A1 | 9/2012 | Carley et al. |
| 2013/0259172 A1 | 10/2013 | Mikhemar et al. |
| 2013/0295172 A1 | 11/2013 | Freeman |
| 2014/0259228 A1 | 9/2014 | Cohen |
| 2015/0265636 A1 | 9/2015 | Kane et al. |
| 2016/0279073 A1* | 9/2016 | Donsky ............... A61K 36/185 |

FOREIGN PATENT DOCUMENTS

| | | |
|---|---|---|
| WO | 97/36577 A1 | 10/1997 |
| WO | 02/080883 A2 | 10/2002 |
| WO | 2004/069180 A2 | 8/2004 |
| WO | 2013009928 A1 | 1/2013 |
| WO | 2015068052 A2 | 5/2015 |

* cited by examiner

*Primary Examiner* — Shobha Kantamneni
(74) *Attorney, Agent, or Firm* — Browdy and Neimark, PLLC

(57) ABSTRACT

Provided is a composition for oral administration which includes a lipophilic active substance and a phospholipid, providing a prolonged therapeutic effect.

24 Claims, 5 Drawing Sheets

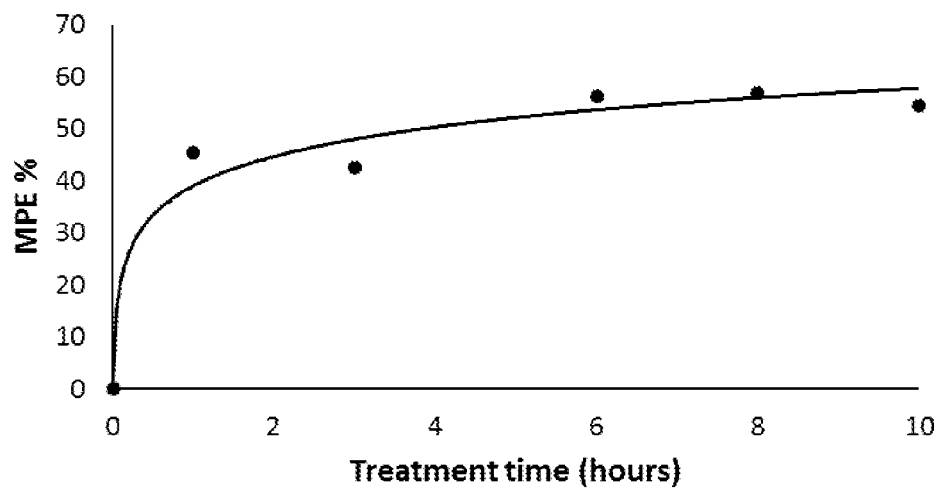
Fig. 1
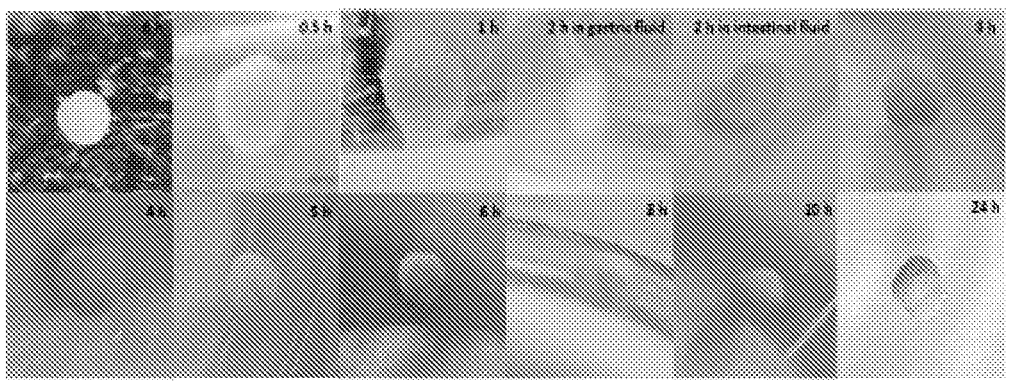
Fig. 2A  Fig. 2B  Fig. 2C  Fig. 2D  Fig. 2E  Fig. 2F
Fig. 2G  Fig. 2H  Fig 2I  Fig. 2J  Fig. 2K  Fig. 2L Fig. 3A    Fig. 3B    Fig. 3C    Fig. 3D    Fig. 3E    Fig. 3F
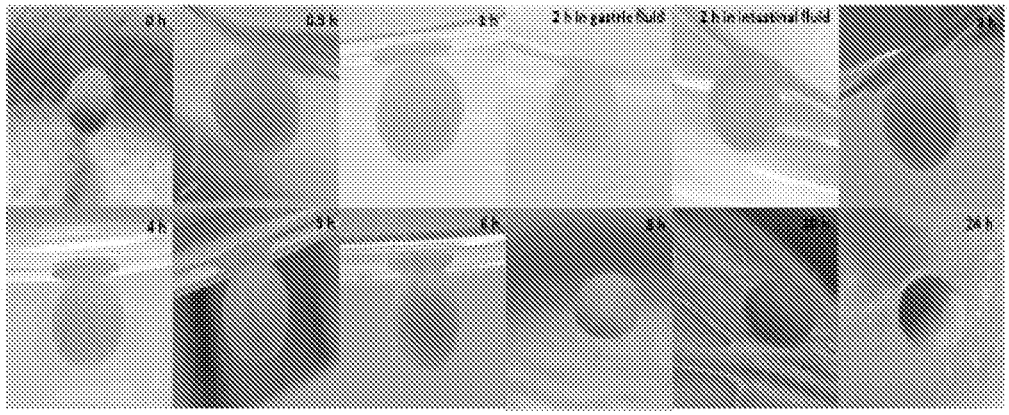
Fig. 3G    Fig. 3H    Fig 3I    Fig. 3J    Fig. 3K    Fig. 3L
Fig. 4A    Fig. 4B    Fig. 4C    Fig. 4D    Fig. 4E    Fig.4F
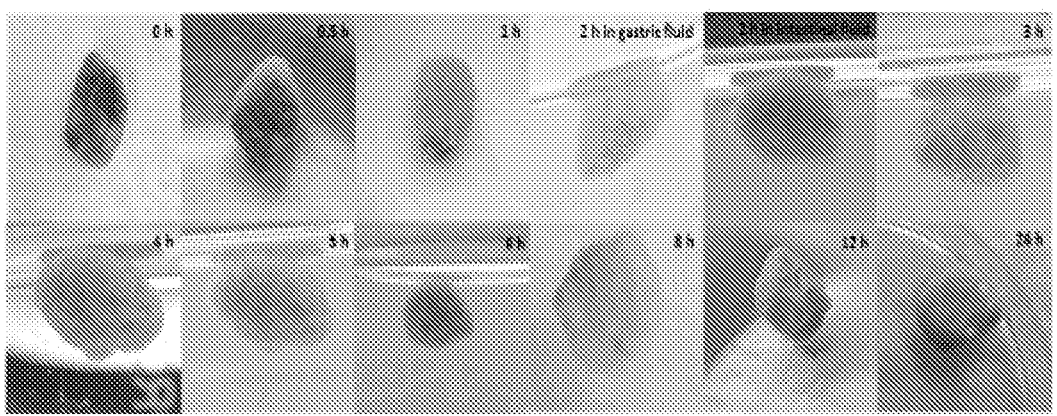
Fig. 4G    Fig. 4H    Fig. 4I    Fig. 4J    Fig. 4K    Fig. 4L Fig. 5A    Fig. 5B    Fig. 5C
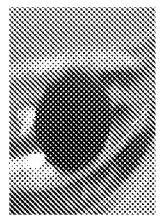 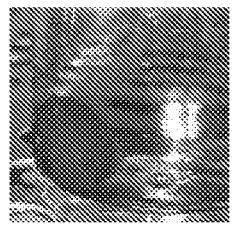 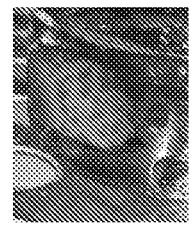
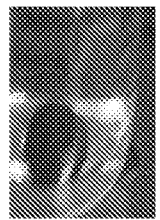 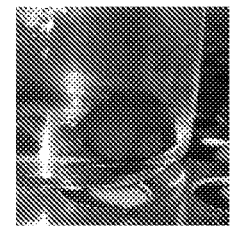 
Fig. 5D    Fig. 5E    Fig. 5F

COMPOSITIONS OF THERAPEUTIC SUBSTANCES, METHODS AND USES THEREOF

TECHNOLOGICAL FIELD

The present invention relates to compositions of lipophilic materials, particularly those adapted for oral administration.

BACKGROUND OF THE INVENTION

There are a number of oral formulations of cannabinoids commercially available by prescription for specific clinical indications. For example, Marinol oil capsules containing as an active ingredient a synthetic $\Delta^9$-THC dissolved in sesame oil having an immediate effect was approved for the control of nausea and vomiting associated with chemotherapy and for appetite stimulation in AIDS patients suffering from wasting syndrome. The manufacture process of Marinol is complex and expensive, and more importantly disadvantageous for the $\Delta^9$-THC stability as it involves application of heat and/or gelation. $\Delta^9$-THC is liable to oxidation, and upon contact with air undergoes gradual oxidation to CBN. Moreover, oil formulations of $\Delta^9$-THC exhibit full therapeutic potency up to 4 hours following administration, with a median $T_{max}$ up to 2.5 hours.

A different formulation, Namisol, as sublingual tablets containing a pure natural $\Delta^9$-THC has been approved for Alzheimer's disease and chronic neural pain. Namisol tablets have a relatively efficient uptake through the sublingual mucosa, however have to be kept under the tongue for the time it takes to dissolve, which makes it difficult for patients to avoid swallowing the tablet when substantial amounts of saliva are produced.

Nabilone (marketed as Cesamet) is a THC mimetic formulated in capsules suitable for oral administration, approved for use as an antiemetic and analgesic for neuropathic pain.

Sativex is a mouth spray containing THC and CBD approved for the treatment of spasticity due to multiple sclerosis.

Some attempts to design sustained release dosage forms have been made, for the most part using oil as the major excipient.

International application publication no. WO 97/36577 describes mixing of lipophilic substances of poor oral bioavailability with at least one solid fat and a phospholipid to obtain a dried solid composition suitable as an oral dosage form.

US Patent application having a publication no. 2012/231083 discloses a medicament essentially containing cannabinoids in a lipophilic medium, such as an oil or oil-based carrier.

International application publication no. WO 04/069180 describes water-dispersible solid compositions of sparingly water-soluble compounds, in a particular lipidic carrier, which upon exposure to gastric and intestinal fluids form micelle dispersions of the sparingly water-soluble compounds.

International application publication no. WO 02/080883 describes compositions for forming molecular associates with lipophilic compounds and methods of loading lipophilic biologically active compounds into previously formed, aqueous suspensions of lipid particles.

BACKGROUND ART

[1] WO 97/36577
[2] US2012231083
[3] WO04069180
[4] WO02080883

SUMMARY OF THE INVENTION

The present disclosure is directed to oral formulations of lipophilic active substances, such as cannabinoids having efficient immediate and prolonged therapeutic effects, without causing GI irritation.

In accordance with aspects, the invention provides a composition for oral administration, the composition comprising at least one lipophilic active substance and at least one phospholipid, and being essentially free of fat glycerides, the composition providing a prolonged therapeutic effect. In some embodiments, the composition being essentially free of solvent(s). In some other embodiments, the composition comprises up to 15% solvent(s).

In accordance with additional aspects, the present invention provides a solid or semisolid oral formulation consisting of at least one cannabinoid and at least one carrier, wherein the at least one cannabinoid is solubilized in the solid carrier, the carrier comprising at least about 60% of at least one phospholipid.

In accordance with further aspects, the present disclosure provides a semisolid, solid and/or solvent-free composition for oral administration, the composition comprising at least one cannabinoid and at least one phospholipid, and being free of fat glycerides, the composition providing an immediate and/or prolonged therapeutic effect.

In accordance with other aspects, the present invention provides a method for producing an immediate effect and/or a prolonged effect associated with at least one lipophilic active substance in a mammal, the method comprising oral administering to the mammal a solid or semisolid composition comprising at least one lipophilic therapeutically active substance and at least one phospholipid, the composition being free of fat glycerides. In some embodiments, the composition being essentially free of solvent(s). In some other embodiments, the composition comprises up to 15% solvent(s).

In accordance with further aspects, the present invention provides a method for preparing a composition comprising at least one lipophilic active substance and at least one phospholipid, the composition being adapted for oral administration, the method comprising:

(a) mixing at least one lipophilic active substance and at least one phospholipid at a w/w ratio selected to produce a solid or semisolid and/or solvent-free mass, the mass being free of fat glycerides, and (b) cutting, shaping, extruding or encapsulating the mass obtained in step (a), in hard or soft gelatin capsules, or molding the mass of step (a) to produce a plurality of dosage forms for oral administration, each of said dosage forms comprising an effective amount of the at least one lipophilic active substance.

The capsules of the invention or those formed according to the invention, may be formed coated with a functional film or a non-functional film. The films may be of or comprising sugar, glazer, polymers, such as acrylates, polyacrylates, Eudragits, celluloses, cellulose derivatives, chitosans, gelatin, wax, or any other coating suitable for oral administration.

The composition or formulation of the invention may be extruded and encapsulated in hard gelatin capsules or polymer capsules. In some embodiments, the capsules are optionally coated with films for achieving specific pH disintegration.

In accordance with further aspects, the present invention provides a dosage form unit or composition comprising a plurality of said units, the dosage form unit comprising at least one lipophilic active substance and at least one phospholipid and being free of fat glycerides, the composition obtained by a method comprising:

(a) mixing at least one lipophilic active substance and at least one phospholipid at a w/w ratio selected to produce a solid or semisolid and/or solvent-free mass, the mass being free of fat glycerides, and (b) cutting, shaping, extruding or encapsulating the mass obtained in step (a), in hard or soft gelatin capsules, or molding the mass of step (a) to produce a plurality of dosage form units for oral administration, each of said dosage form units comprising an effective amount of the at least one lipophilic active substance.

In accordance with further aspects, the present invention provides a kit for preparing an oral composition comprising at least one lipophilic active substance and at least one phospholipid, the kit comprising (a) at least one lipophilic active substance, in a first unit dosage form, (b) at least one phospholipid, in a second unit dosage form; and optionally (c) a container for mixing (a) and (b), the kit being free of fat glycerides and comprising instructions of use.

In accordance with further aspects, the present invention provides a method for treating or ameliorating at least one symptom associated with at least one disease or disorder in a mammal, the method comprising oral administering to the mammal an effective amount of a solid oral formulation or semisolid oral formulation, the formulation comprising at least one lipophilic active substance and at least one phospholipid, the formulation being free of fat glycerides. In some embodiments, the solid oral formulation or the semisolid oral formulation is essentially free of solvent(s). In some other embodiments, the solid oral formulation or the semisolid oral formulation comprises up to 15% solvent(s).

As appreciated, the cannabinoid compositions described herein provide means to achieve a number of clinically relevant applications, which are unique, such as new dosage forms for oral drug delivery and methods for producing immediate and/or prolonged release of the drug. Furthermore, the present disclosure may be extrapolated to oral compositions of other lipophilic therapeutically active substances to circumvent problems of decreased dissolution, bioavailability, absorption, and short-term therapeutic effects. The novel compositions are also easy to make, eco-friendly, and affordable in terms of process of manufacture.

BRIEF DESCRIPTION OF THE DRAWINGS

FIG. 1 is a graph showing % MPE values in mice treated with 50 mg/kg CBD per os in a formulation according with the present disclosure.

FIGS. 2A-2L provide images of the results of Example 7, showing the behavior of a dosage form according with some embodiments of the invention, comprising Phospholipon (PL) carrier and cannabidiol (CBD) in a ratio of 6:4, incubated in simulated gastric fluid at 37° C. for 2 h followed by incubation in intestinal fluid at 37° C. for additional 24 h: FIG. 2A—before incubation, FIG. 2B—0.5 h after incubation in simulated gastric fluid, FIG. 2C—1 h after incubation in simulated gastric fluid, FIG. 2D—2 h after incubation in simulated gastric fluid, FIG. 2E—2 h after incubation in intestinal fluid, FIG. 2F—3 h after incubation in intestinal fluid, FIG. 2G—4 h after incubation in intestinal fluid, FIG. 2H—5 h after incubation in intestinal fluid, FIG. 2I—6 h after incubation in intestinal fluid, FIG. 2J—8 h after incubation in intestinal fluid, FIG. 2K—10 h after incubation in intestinal fluid, and FIG. 2L—24 h after incubation in intestinal fluid.

FIGS. 3A-3L provide images of the results of Example 7, showing the behavior of a dosage form according with some embodiments, comprising PL carrier and CBD in a ratio of 7:3, incubated in simulated gastric fluid at 37° C. for 2 h followed by an incubation in intestinal fluid at 37° C. for an additional 24 h: FIG. 3A—before incubation, FIG. 3B—0.5 h after incubation in simulated gastric fluid, FIG. 3C—1 h after incubation in simulated gastric fluid, FIG. 3D—2 h after incubation in simulated gastric fluid, FIG. 3E—2 h after incubation in intestinal fluid, FIG. 3F—3 h after incubation in intestinal fluid, FIG. 3G—4 h after incubation in intestinal fluid, FIG. 3H—5 h after incubation in intestinal fluid, FIG. 3I—6 h after incubation in intestinal fluid, FIG. 3J—8 h after incubation in intestinal fluid, FIG. 3K—10 h after incubation in intestinal fluid, and FIG. 3L—24 h after incubation in intestinal fluid.

FIGS. 4A-4L provide images showing behavior of a dosage form according with some embodiments, comprising PL carrier and tetrahydrocannabinol (THC) at a ratio of 9:1, incubated in simulated gastric fluid at 37° C. for 2 h followed by incubation in intestinal fluid at 37° C. for an additional 24 h: FIG. 4A—before incubation, FIG. 4B—0.5 h after incubation in simulated gastric fluid, FIG. 4C—1 h after incubation in simulated gastric fluid, FIG. 4D—2 h after incubation in simulated gastric fluid, FIG. 4E—2 h after incubation in intestinal fluid, FIG. 4F—3 h after incubation in intestinal fluid, FIG. 4G—4 h after incubation in intestinal fluid, FIG. 4H—5 h after incubation in intestinal fluid, FIG. 4I—6 h after incubation in intestinal fluid, FIG. 4J—8 h after incubation in intestinal fluid, FIG. 4K—10 h after incubation in intestinal fluid, and FIG. 4L—24 h after incubation in intestinal fluid.

FIGS. 5A-5F provide images showing behavior of a dosage form comprising Sudan III and a PL carrier at a ratio of 0.1:9.9 (FIGS. 5A to 5C) or 1:9 (FIGS. 5D to 5F), incubated in simulated gastric fluid at 37° C. for 48 h, FIGS. 5A and 5D before incubation (control), FIGS. 5B and 5E—4 h after incubation in simulated gastric fluid, and FIGS. 5C and 5F—48 h after incubation in simulated gastric fluid, FIGS. 6A-6B provide images showing initial appearance of formulation according with the present disclosure (FIG. 6A) and of a control (FIG. 6B).

FIG. 7A—before incubation, FIG. 7B—1 h after incubation in simulated gastric fluid, FIG. 7C—2 h after incubation in simulated gastric fluid, FIG. 7D—10 h after incubation in simulated intestinal fluid at 37° C., FIGS. 8A-8D provide images showing the behavior of capsule containing control formulation at different time points after incubation.

DETAILED DESCRIPTION OF EMBODIMENTS

Figure 6A:
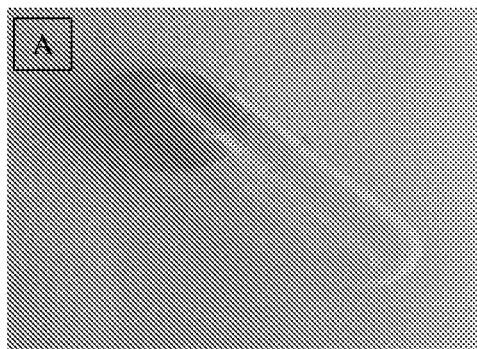

Use of lipophilic substances having prolonged/delayed effect via oral administration is often challenging due to the low water solubility of these substances, which may result in poor bioavailability and short time effect. The inventor has found that compositions comprising lipophilic active substances such as cannabinoids and phospholipids, as the main excipient, are suitable for oral administration, possessing surprising therapeutic effects that may be immediate and prolonged, without needing to employ fats, oils or chemical solvents.

The present invention provides a composition for oral administration, the composition comprising at least one lipophilic active substance and at least one phospholipid, the composition being essentially free of fat glycerides.

The composition according to the present disclosure may be solvent free, namely does not comprise a solvent or it may comprise up to 15% solvent(s). In some other embodiments, the composition is free of any solvents.

Compositions and formulations according to the present invention are generally prepared by mixing the at least one lipophilic active substance and the at least one phospholipid at a w/w ratio suitable to produce a solid, semisolid mass that is free of fat glycerides. Once the mass has been formed, it may be cut, shaped, encapsulated in a gelatin capsule or otherwise manipulated to produce a plurality of dosage form units that are suitable for oral administration. Each of the units comprised an effective amount of the at least one lipophilic active substance. In some embodiments, the solid, semisolid and/or mass being essentially free of solvent. In some other embodiments, the solid, semisolid and/or mass comprises up to 15% solvent(s).

Thus, the term "solvent free" denotes a composition of the invention which is free of any one or more water-based or organic solvents, either polar or non-polar.

In some embodiments, the composition comprising up to 15% solvent. At times, the composition comprises between 0% (solvent free) to about 15% solvent, at times between 0% solvent to about 10% solvent, at times even between 0% to about 5% solvent. It should be noted that a composition comprising 0% solvent is considered as a solvent free composition.

The solvent may be any one or more of pentane, hexane, cyclohexane, benzene, toluene, chloroform, diethyl ether, n-propanol, iso-propyl alcohol, ethanol, propylene glycol, polyethylene glycol, methanol, DMSO, THF, DMF, dioxane, dichloromethane, ethyl acetate, acetone, tetrachloroethylene and water.

In some embodiments, may be any one or more of n-propanol, iso-propyl alcohol, ethanol, propylene glycol, polyethylene glycol, DMSO and water.

In some further embodiments, the solvent is a hydrophilic solvent. The hydrophilic solvent may be any one of water, glycol, alcohol or any combination thereof.

An additional unique feature of the compositions of the invention is in being free of fat, such as solid fat for example glycerides, natural or synthetic. Vegetable oils and animal fats contain mostly triglycerides. Medium Chain Triglycerides (MCTs), i.e., which fatty acids have an aliphatic tail of 6-12 carbon atoms, are commonly used to facilitate solubility of lipophilic drugs. Thus, the compositions described herein are essentially free of triglycerides.

The present invention further provides a composition for oral administration, the composition comprising at least one lipophilic active substance and at least one phospholipid, the composition being free of fat glycerides having a prolong effect. As shown herein below in the Examples, the composition of the present disclosure was found to exhibit prolonged therapeutic effect. Thus, compositions according to the invention, by virtue of their constituents and method of preparation, are formulated in a form adapted for oral administration.

In some embodiments, the compositions of the invention are solid or semisolid compositions. The term "semisolid" refers to a form which on one hand supports its own weight and holds its shape and on the other hand is capable of conforming in shape.

The at least one 'lipophilic active substance' is one or more therapeutically active substance, drug, additive, food additive, vitamin, supplement, and others exhibiting poor or low solubility in water, and which is preferentially soluble in fats, oils, lipids, and non-polar solvents. In some embodiments, the at least one lipophilic active substance has a solubility of less than 0.5%, 0.4%, 0.3%, 0.2% or 0.1%, by weight, in water at 20° C.

In some embodiments, the lipophilic active substance is a drug. In some other embodiments, the lipophilic active substance is a lipophilic drug.

In some further embodiments, the lipophilic active substance is a lipophilic oral drug belonging to the General Drug Categories classified by the FDA according to their clinical effects and applicability to most common human disorders.

The lipophilic active substance may be an active ingredient of Class II or Class IV of the Biopharmaceutics Classification System (BCS). Non-limiting example of such lipophilic active substances include cannabinoids, anti-epileptics, drugs used in the treatment of Alzheimer disease, drugs used in the treatment of multiple sclerosis, drugs used in the treatment of LS, anti-spastics, drugs used in the treatment of autism, drugs used in the treatment of epilepsy, drugs used in the treatment of IBD, drugs used in the treatment of Crohn's disease, analgesics, antacids, antianxiety drugs, anti-arrhythmics, anti-bacterials, antibiotics, antimicotics, anticoagulants and thrombolytics, anticonvulsants, antidepressants, antidiarrheals, antiemetics, antifungals, antihistamines, anti-hypertensives, anti-inflammatories, antineoplastics, antipsychotics, antipyretics, antivirals, barbiturates, beta-blockers, bronchodilators, cold cures, cholesterol lowering drugs, corticosteroids, cough suppressants, cytotoxics, decongestants, diuretics, expectorant, hormones, hypoglycemics, immune-suppressives, laxatives, muscle relaxants, sedatives, sex hormones, sleeping drugs, tranquilizer and vitamin supplements, such as omega fatty acids, omega-3-fatty acids, EPA, DHA or ALA.

In some embodiments, the lipophilic active substance is selected from nifedipine (hypertension), amitriptyline (an antidepressant), rotigotine (Parkinson's disease), fentanyl (an anesthetic), nitroglycerin (coronary artery disease), menthol (pain relief), ibuprofen (antipyretic, anti-inflammatory, pain relief), simvastatin (cholesterol lowering drug), terpinoids or terpens (cancer, mycotic and microbial infection), lycopene, and lipophilic vitamins such as vitamins A, D, E, and K.

In some embodiments, the lipophilic active substance is hemp seed oil or hash oil.

In some embodiments, the lipophilic active substance comprise or consists at least one cannabinoid. As known in the art, the 'cannabinoids' are a class of chemical compounds that act on cannabinoid (CB) receptors. In some embodiments, the lipophilic active substance is selected based on its binding to a cannabinoid receptor in cells, such as cannabinoid receptor type 1 or cannabinoid receptor type 2.

In some embodiments, the at least one cannabinoid is selected from natural and synthetic cannabinoid. In some embodiments, the cannabinoid is selected from endocannabinoid (produced naturally by humans and animals), phytocannabinoid (found in *cannabis* and some other plants) and synthetic cannabinoids (manufactured artificially). In some embodiments, the at least one cannabinoid is a dried whole extract comprising a cannabinoid, hemp seed oil or hash oil. Such an extract may be obtained by any known method in the field.

In some embodiments, the at least one cannabinoid is an extract from the seeds, flowers, and/or any part of a *cannabis* plant species (*Sativa, Indica*), whether naturally occurring or not. In some embodiments, the *cannabis* plant is disclosed in US Plant Patent Application No. 2016/0073566, known also as *Avidekel*. US Plant Patent Application No. 2016/0073566 is herein incorporated by reference.

In some embodiments, the at least one cannabinoid is selected from tetrahydrocannabinol (THC), cannabidiol (CBD), cannabinol (CBN), cannabigerol (CBG), cannabichromene (CBC), cannabivarin (CBV), cannabielsoin (CBE), cannabicyclol (CBL), tetrahydrocannabivarin (THCV), cannabichromevarin (CBDV), cannabichromevarin (CBCV), cannabigerovarin (CBGV), cannabigerol monomethyl ether (CBGM), iso-tetrahydrocannabinol (iso-THC) and their respective 2-carboxylic acids (2-COOH) or any combination thereof.

The "THC" and "CBD" may be used as known in the art, and thus may also encompass any one or more isomer, derivative or precursor thereof; these include for, example, (−)-trans-Δ9-tetrahydrocannabinol (Δ9-THC), Δ8-THC, and Δ9-CBD, and further to THC and CBD derived from their respective 2-carboxylic acids (2-COOH), THC-A and CBD-A.

In some embodiments, the at least one cannabinoid is CBD or any one or more isomer, derivative or precursor thereof.

In some further embodiments, the at least one cannabinoid is THC or any one or more isomer, derivative or precursor thereof.

In some further embodiments, the lipophilic active substance comprise a combination of two or more cannabinoids. In some embodiments, the combination is of THC and one or more cannabinoids. In some embodiments, the combination is of CBD and one or more cannabinoids. In some embodiments, the combination is of THC and CBD.

In some embodiments, the lipophilic active substance comprise hemp oil (also denoted hempseed oil) or hash oil.

As appreciated, in case a combination of two or more lipophilic active substances is present in a composition, various amounts of the different substances may be used. For example, in the case of a combination of CBD and THC, the w/w ratio between the two may be at least 1:1, 5:1, at least 10:1, at least 30:1, at least 50:1, at least 100:1, or at least 200:1. These ratios are similarly relevant to other combinations, e.g., of CBD with at least one lipophilic active substance.

As described herein, the present disclosure provides compositions comprising cannabinoids, such as CBD, THC or combinations thereof, with at least one phospholipid. The at least one 'phospholipid' used in compositions of the invention is a material as known in the art, having amphiphilic characteristics comprising a hydrophilic head and a hydrophobic tail, with the hydrophilic part comprising a phosphate group and the hydrophobic part comprising two fatty acids, which may or may not be the same. The phosphate group may be modified with an organic molecule such as choline, ethanolamine, serine or inositol.

The phospholipid may be selected from natural sources such a vegetable source (soy phospholipid, rapeseed (canola) or sunflower), or an animal source (egg phospholipid) or may be synthetic or semi-synthetic (naturally based, yet chemically modified). Further, the phospholipid may be selected from hydrogenated phospholipids and non-hydrogenated phospholipids. In some embodiments, the at least one phospholipid is a non-hydrogenated phospholipid or a phospholipid combination comprising at least one non-hydrogenated phospholipid.

Non-limiting examples of phospholipids include glycerophospholipid, phosphatidic acid (PA), phosphatidylcholine (PC), phosphatidylinositol (PI), phosphatidylserine (PS), phosphatidylethanolamine (PE), phosphatidylglycerol (PG), cardiolipin (CL), phosphosphingolipid, phosphoinositide, phospholipons, lipoids, lecithins and ceramides.

In some other embodiments, the phospholipid is a phosphosphingolipid. In some embodiments, the phosphosphingolipid is sphingomyelin.

In some embodiments, the phospholipid is selected amongst hydrogenated phospholipids, such as phosphatidylcholine (commercially available under "Phospholipon® 90 H" or Phospholipon® 80 H"). In some embodiments, the phospholipid is or comprises pure phosphatidylcholine (commercially available under "Phospholipon® 90 G" or "Phospholipon® 80 G"), Lipoid S100, Lipoid S PC, Lipoid S75, Lipoids E 80, Lipoids PC, Lipoids E. In some further embodiments, the phospholipid is or comprises phosphatidylcholine from soybean (commercially available under "Lipoid S 100®").

In some embodiments, the composition comprises at least one cannabinoid and a hydrogenated phosphatidylcholine. In some embodiments, the composition comprises at least one cannabinoid and phosphatidylcholine (pure, non-hydrogenated). In some other embodiments, the composition comprises at least one cannabinoid, a hydrogenated phosphatidylcholine and phosphatidylcholine (pure, non-hydrogenated).

In some embodiments, the composition comprises CBD and a hydrogenated phosphatidylcholine. In some other embodiments, the composition comprises CBD and phosphatidylcholine (pure, non-hydrogenated). In some further embodiments, the composition comprises at least CBD, hydrogenated phosphatidylcholine and phosphatidylcholine (pure, non-hydrogenated).

In some embodiments, the composition comprises THC and a hydrogenated phosphatidylcholine. In some other embodiments, the composition comprises THC and phosphatidylcholine (e.g., pure, non-hydrogenated). In some further embodiments, the composition comprises THC, hydrogenated phosphatidylcholine and phosphatidylcholine (e.g., pure, non-hydrogenated).

In some embodiments, the composition comprises a mixture of cannabinoids and a hydrogenated phosphatidylcholine. In some other embodiments, the composition comprises a mixture of cannabinoids and phosphatidylcholine (e.g., pure, non-hydrogenated).

In some embodiments, the composition comprises CBD and Phospholipon® 90 H. In some embodiments, the composition comprises CBD and Phospholipon® 90 G. In some further embodiments, the composition comprises CBD, Phospholipon® 90 H and Phospholipon® 90G. In some embodiments, the composition comprises Lipoid S100 and cannabinoids. In some embodiments, the composition comprises Lipoid S and cannabinoids. In some further embodiments, the phospholipid is or comprises phosphatidylcholine from soybean (commercially available under "Lipoid S 100®").

In some embodiments, the composition comprises CBD, THC and a hydrogenated phosphatidylcholine. In some embodiments, the composition comprises CBD, THC and phosphatidylcholine (pure, non-hydrogenated). In some further embodiments, the composition comprises CBD, THC, hydrogenated phosphatidylcholine and phosphatidylcholine (pure, non-hydrogenated).

In some embodiments, the composition comprises CBD, THC and Phospholipon® 90 H. In some other embodiments, the composition comprises CBD, THC and Phospholipon® 90 G. In some further embodiments, the composition comprises CBD, THC, Phospholipon® 90 H and Phospholipon® 90 G. In some embodiments, the composition comprises CBD, THC and Lipoid S or Lipoid S100® or their mixture.

The novel compositions described herein comprise at least one lipophilic active substance and at least one phospholipid at varying weight per weight (w/w) ratio. This is to convey that the compositions of the invention may comprise various amounts of the lipophilic drug(s) as compared with the phospholipid(s), expressed in w/w percent as at least about 0.0001%, 0.001%, 0.01%, 0.1%, 1%, 2%, 3%, 4%, 5%, 6%, 7%, 8%, 9%, 10%, and further up to 15%, 20%, 30%, 40%, 50%, 60%, 70%, 80%, 90, 100% and up to 200% lipophilic drug(s) versus phospholipid(s).

This particular feature may be further articulated as that the compositions of the invention may comprise at least one lipophilic active substance and at least one phospholipid at a w/w ratio of at least about 0.0001, 0.001, 0.01, 0.1, 1 and 2, respectively, including all intermediate proportions.

In some embodiments, the composition comprises at least one lipophilic active substance and at least one phospholipid at a weight per weight (w/w) ratio in the range of about 0.01:99.99 to 2:1, respectively. In some embodiments, the ratio is 1:1.

Still further, it may be further articulated as that the compositions of the invention may comprise the at least one lipophilic active in a minimal w/w ratio of at least about 0.0001 or more, or a maximal w/w ratio of at least about 2 or less, respective to the amount of the phospholipid. In some embodiments, the cannabinoid compositions may comprise at least one cannabinoid and at least one phospholipid at a minimal w/w ratio of at least about 0.0001 or more, or a maximal w/w ratio of at least about 2 or less, respectively.

In terms of proportions between the constituents, the cannabinoid compositions may comprise at least one cannabinoid and at least one phospholipid at a w/w ratio of at least about 0.0001, 0.001, 0.01, 0.1, 1 and 2, respectively, including all intermediate proportions.

In some embodiments, the ratio of at least one lipophilic subtenant to the at least one phospholipid is 1:9 or 2:8. In some embodiments, the at least one lipophilic substance is THC, CBD or a combination thereof.

In other embodiments, the cannabinoid compositions may comprise at least one cannabinoid and at least one phospholipid at a w/w ratio in the range of at least about 0.01 to 1.

An important aspect of the invention rooted in the particular qualities of the mass, may be articulated as a solid or a semisolid therapeutic dosage form comprising an amount of at least one lipophilic therapeutically active substance and at least one phospholipid, in the absence of fat glycerides. The therapeutic dosage form may be adapted for forming individual doses for oral administration, each dose comprising an effective amount of the at least one lipophilic therapeutically active substance.

In other words, the present invention provides a novel formulation, produced en masse, comprising one or more drug components, which may be divided and shaped into separate therapeutic dosage forms, adapted for oral administration and/or individual dosing regimen. The mixture of the drug(s) and phospholipid(s), the latter being the main and important excipient in the composition, a compact mass is formed that can be shaped to different sizes and geometries adequate for swallowing.

In some embodiments, the invention provides a solid and/or semisolid composition for oral administration consisting of at least one lipophilic therapeutically active substance and at least one phospholipid. In some embodiments, the compositions of the invention constitute a solid and/or semisolid formulation consisting of at least one cannabinoid and at least one non-liquid carrier, wherein the at least one cannabinoid is dissolved in the non-liquid carrier, the carrier comprising at least about 60%, at times at least 70% of the at least one phospholipid. In some embodiments, the carrier comprises at least about 80%, 85%, 90%, 95%, 96%, 97%, 98% or 99% of at least one phospholipid.

It is thus contemplated that the present invention provides novel dosage form for oral delivery of lipophilic drugs. Specific features of this new dosage form are discussed herein below in the context of a drug delivery system. It should be noted that this novel dosage form is particularly adaptable for individual preferences and individual optimization of therapeutic drug dosing. As shown in the examples below, the dosage forms formulated and constructed according with the present disclosure, did not disintegrated after incubation in both a gastric fluid medium and an intestinal fluid medium. Further and as shown below, compositions of the invention, when packaged in hard gelatin capsules did not disintegrate as compared with capsules containing a control composition and olive oil.

As described herein, the composition of the present disclosure are prepared by mixing the at least one lipophilic active substance with at least one phospholipid without the need to add any fat or solvent in order to dissolve the at least one lipophilic active substance. This is highly advantage over methods described in the art as no evaporation of a solvent to dryness is required in the preparation. In some embodiments, the method described herein may comprise a step of filling a capsule or a solid carrier with the mass produced by mixing at least one lipophilic active substance and at least one phospholipid. The filling may be by any means available in the art.

In some embodiments, the shaping of a mass may be achievable by extrusion. In some embodiments, the mass is molded in molds of specific forms. In some embodiments, molding is achievable at a temperature below 100° C. In some embodiments, molding is carried out at room temperature (between 25° C. and 30° C.). In some embodiments, the mass is produced using machinery and technology for candy manufacture, chocolate manufacture, soft gel encapsulation, capsule filing, soft capsule filing, shell gelatin, starch molds, sugar coating and/or wax coating. In some embodiments, the mass is treated to obtain the final dosage form using machinery and technologies for gel and unit dose gel manufacture. Advantages of the above methods are apparent in being simple, straightforward, and inexpensive, and in being eco-friendly, and most importantly in providing a superior product.

After the mass is formed, it is cut, shaped, molded, or optionally rolled with roller, cut and shaped. The shapes could be any adequate form for oral administration, such as bean, jellybean, ball, sphere, knob, pellet, with a weight from a few mg to hundreds of mgs.

In some embodiments, the method may involve additional steps comprising mixing into the mass at least one an antioxidant, a hardening agent, increase viscosity agent, decrease viscosity agent, a surfactant, surfactant a free-flow imparting agent, a color- and a taste masking agent, a flavor-imparting agent, or a salt, or any combination thereof.

Alternatively, the forms could be optionally coated with sugar, vegetal wax, beeswax, synthetic wax, chocolate coating, glazer, films, polymers, acrylates, polyacrylates, Eudragits, celluloses, cellulose derivatives, chitosans, gelatin, any coating for oral administration.

In some embodiments, the preparation methods may comprise mixing at least one lipophilic active substance and at least one phospholipid in step (a) in a minimal w/w/ ratio of at least about 0.0001 or more, or a maximal w/w ratio of at least about 2 or less, respectively.

Without being bound by theory, it is suggested by the inventor that compositions of lipophilic drugs according to the invention behave as compact 'tankers' or drug reservoirs, in which the drug dissolves in the formulation without the need for aqueous or organic solvents. Upon oral administration and exposure to aqueous environment such as GI, the drug 'tanker' remains intact or disintegrates/erodes slowly. It is noteworthy that the drug incorporated in the 'tanker', when administered orally, exhibits an effect shortly after administration, the effect being maintained for a prolonged period of time.

Without being bound by theory, it is proposed that one of the possible release mechanisms is that the compact 'tanker' hydrates slowly only on the surface, thereby producing layers of phospholipid colloidal entities incorporating the drug. The phospholipid-drug entities diffuse from the surface of the 'tanker' into the bulk of the GI juice and then absorbed in the GI lumen. In other words, due to the particular unique physical and chemical properties this drug reservoir, the drug becomes available immediately and for a prolonged period of time, thereby producing prolonged action kinetics.

The compositions according to the invention by the virtue apart from phospholipid(s), and specifically free of fat glycerides, and further, due to their straightforward method of preparation, possess unique physical and chemical properties underlying their observed short- and long-term pharmacodynamic effects in vivo.

These particular physical and chemical features confer to the compositions of the invention surprising therapeutic qualities, most prominent of which are immediate and prolonged therapeutic effects of the lipophilic drug. Thus, the present invention provides a method for producing immediate and prolonged or prolonged effect of at least one lipophilic therapeutically active substance in a mammal, the method comprising oral administering to the mammal a composition comprising at least one lipophilic therapeutically active substance and at least one phospholipid, in the absence of fat glycerides. Thus, the invention provides a method to modify time-dependent release in oral dose formulations of lipophilic drugs, and particularly to prolong action and/or to maintain effective drug levels.

Most conventional (immediate release) oral drug products, such as tablets and capsules, are formulated to release the active drug immediately after oral administration. In the formulation of conventional drug products, no deliberate effort is made to modify the drug release rate. Immediate-release products generally result in relatively rapid drug absorption and onset of accompanying pharmacodynamic effects. In some embodiments, the method according to any aspect or embodiment of the invention may use oral administering of the compositions comprising at least one lipophilic therapeutically active substance and at least one phospholipid at a minimal w/w ratio of at least about 0.0001 or more, or a maximal w/w ratio of at least about 2 or less, respectively. In some embodiments, the method may use oral administering of specific compositions of the invention that comprise at least one cannabinoid as therapeutically active substance. Applicability of such a method for efficient management of pain is presently exemplified in a paradigm of pain in animal model.

In another aspect of the present disclosure it is provided a method for treating or ameliorating at least one symptom of at least one disorder or a disease in a mammal, the method comprising oral administering to the mammal an effective amount of a solid or semisolid and/or composition comprising at least one lipophilic active substance and at least one phospholipid, the composition being free of fat glycerides.

The present disclosure also provides a semisolid and/or composition comprising at least one lipophilic active substance and at least one phospholipid, the composition being free of fat glycerides for treating or ameliorating at least one symptom of at least one disorder or a disease in a mammal, as disclosed herein. In some embodiments, the composition or a dosage form are for oral administration.

Another aspect of the present invention is to provide use of an effective amount of at least one lipophilic active substance and at least one phospholipid, in the absence of fat glycerides, in the manufacture/preparation of a solid or semisolid and/or oral composition for treating or ameliorating the symptoms of at least one disorder or a disease in a mammal.

The terms 'disorder' or 'disease', as used herein, encompasses a clinical condition diagnosed in a mammalian subject, including humans, by the current and/or internationally accepted diagnostic criteria, such as International Statistical Classification of Diseases and Related Health Problems 10th Revision (ICD10) for human disorder, or Diagnostic and Statistical Manual of Mental Disorders, 4th Edition (DSM-IV) or DSM-IV Text Revision (DSM-IV-TR) for human mental and psychiatric conditions.

In some embodiments, it is contemplated that the therapeutic methods according to the invention are applicable to a wide range of clinical and subclinical conditions, such as those showing at least one symptom of at least one an inflammatory disorder, a neurological disorder, a psychiatric disorder, a malignancy, an immune disorder, a metabolic disorder, an infectious disease, pain, a gastrointestinal disorder, a cardiovascular disorder, a nutritional deficiency.

In some embodiments, the at least one disorder or disease is selected from clinical conditions that are treatable by cannabinoid/cannabinoid agonists/cannabinoid-related compounds. In some embodiments, the at least one disorder or disease is selected from anorexia, emesis, pain, inflammation, multiple sclerosis, neurodegenerative disorders (such as Parkinson's disease, Huntington's disease, Tourette's syndrome, Alzheimer's disease), autism, epilepsy, glaucoma, osteoporosis, schizophrenia, cardiovascular disorders, cancer, obesity, and metabolic syndrome-related disorders, IBD, Crohn's disease and spastic disorders.

In some embodiments, the therapeutic method according to the invention is used for treating pain.

The terms 'treating', 'treatment' or 'therapy' used in accordance with the invention refer equally to curative therapy, prophylactic or preventative therapy and ameliorating therapy. The terms refer to an approach for obtaining beneficial or desired therapeutic effects, which may be established clinically by means of physiological, metabolic or biochemical parameters. In this application of invention, beneficial or desired clinical results include, but are not limited to, alleviation of symptoms, diminishment of extent of disease, stabilized (i.e., not worsening) condition, delay or slowing of progression or worsening of condition/symptoms, amelioration or palliation of the condition or symptoms, inhibition, reduction, attenuation and remission (whether partial or total), whether detectable or undetectable. The term palliation and variations thereof, as used herein, means that the extent and/or undesirable manifestations of a physiological condition or symptom are lessened and/or time course of the progression is slowed or lengthened, as compared to not administering compositions of the present invention.

It should be appreciated that the terms "inhibition", "reduction" or "attenuation", as used herein, relate to the retardation, restraining or reduction of a process or an effect associated with a process, e.g., symptoms, by anywhere between about 1% and 99.9% of the original effect or symptoms. In some embodiments, the retardation, restraining or reduction is between about 1% and about 5%, between about 5% and 10%, between about 10% and 15%, between about 15% and 20%, between about 20% and 25%, between about 25% and 30%, between about 30% and 35%, between about 35% and 40%, between about 40% and 45%, between about 45% and 50%, between about 50% and 55%, between about 55% and 60%, between about 60% and 65%, between about 65% and 70%, between about 75% and 80%, between about 80% and 85%, between about 85% and 90%, between about 90% and 95%, between about 95% and 99%, or between about 99% and 99.9%.

Generally, the term 'therapeutic effect' means any change in a condition treated by a composition of the invention, as measured by the relevant definition criteria, being it changes in a condition monitored in an animal model or in the clinical setting. In this sense, the therapeutic effect is also a pharmaco-dymanic effect, measured in an experimental or a clinical setting in vivo. In some embodiments, a change in the condition being treated is identified if there is at least 5% improvement, at time at least 10% improvement, at times at least 25%, or at times at least 50%, or at times at least 75%, or at times at least 100% improvement. The change can be based on improvements in the severity of the treated condition in an individual, or on a difference in the frequency of improved conditions in populations of subjects with and without treatment with the compositions of the invention, or with the compositions of the invention in combination with other drugs.

In the context of the invention, a prolonged therapeutic effect is one which persists for a longer period, such as the analgesic effect of cannabinoid, such as CBD, THC or any combination thereof, tested in acetic-acid writhing test that persisted for 10 hours, in fact, until termination of the experiment. It is thus conceivable that a prolong therapeutic effect of the compositions of the invention may persist for at least about up to 3 hours, 6 hours, 12 hours, 18 hours, 24 hours, and further more than 1 day, and 2, 3, 5, 6, 7, 8, 9, 10 days and more. As shown in the examples below, oral administration of compositions comprising CBD and a phospholipid (e.g., Phospholipon) led to pronounced immediate analgesic effect which was maintained as a plateau for at least 10 hours. Further, as shown, combination of THC and CBD, such that CBD is present at high concentrations (even 100 times) compared with THC, produced an immediate and prolong effect.

It should be noted that the prolonged therapeutic effect may be referred to a specific therapeutic effect (for example analgesic effect) that is maintained for a time period longer than an effect produced with a conventional treatment or as compared with treatment by a cannabinoid.

As used herein, the terms 'therapeutic drug dose', 'therapeutically effective drug dose' 'effective drug dose' and 'therapeutically effective amount' are interchangeable (also pharmacologically or pharmaceutically or physiologically effective amount), and relate to the amount of a drug present in a pharmaceutical composition that is needed to provide a desired level of the active agent in the bloodstream or at the target organ of an organism to be treated, so as to yield or endow an anticipated physiological response when administered. The precise amount will depend upon numerous factors, e.g., the active agent, the activity of the composition, the delivery device employed, the physical characteristics of the composition, intended patient use (i.e., the number of doses administered per day), patient considerations, and the like, and can readily be determined by one skilled in the art, based upon the information provided herein. The term 'therapeutically effective amount' refers to an amount of from about 10 mcg to about 1000 mg composition per kg body weight of the subject treated by this method per day. Further, this range can be from several micrograms (mcg), e.g., from 10, 25, 50, 75, 100, 150, 200, 300 mcg per day up to 400, 450, 500, 550, 60, 650, 700, 750, 800, 850, 900, 950 and 100 mg/kg/day.

An effective amount of a drug can be administered in one administration, or through multiple administrations of an amount that total an effective amount, e.g., within a 24-hour period. It can be determined using standard clinical procedures for determining appropriate amounts and timing of administration. It is understood that the effective amount can be the result of empirical and/or individualized (case-by-case) determination on the part of the treating health care professional and/or individual. Several dosing methods have been developed including use of 'standard' doses, population-based predictive algorithms and nomograms, pharmacokinetic equations, and Bayesian feedback.

It should be further appreciated that for the purpose of the invention this term also refers to an individualized therapeutically effective amount. Methods for establishing to an individualized therapeutically effective amount have been referred to above. One common method is by 'trial and error' starting from a minimal or a standard dose, under the supervision of a treating physician.

Still further, it is conceived that in some embodiments the therapeutic methods according to the invention may involve combination therapies. In other words, that the oral compositions of the invention may be administered in combination with one or more additional compounds or therapies, the latter using enteral or parenteral and include, but are not limited to, intradermal, intramuscular, intraperitoneal, intravenous, subcutaneous, intranasal, epidural, vaginal, rectal, transdermal and oral administration routes.

In some embodiments, the therapeutic methods according to the above may use an oral composition comprising at least one lipophilic therapeutically active substance and at least one phospholipid at a minimal w/w ratio of at least about 0.0001 or more, or a maximal w/w ratio of at least about 2 or less, respectively.

In further embodiments, the therapeutic methods according to the invention may use an oral composition of the invention comprising as least one lipophilic active substance at least one cannabinoid.

Considering the present level of knowledge with respect to the clinical applications of cannabinoids in young and elderly patients, it is conceived the cannabinoid composition according to the invention may be applicable, although not only, to at least one of depression, sleeping disorders, eating disorders, multiple sclerosis, Parkinson, epilepsy, autism, cancer, appetite stimulant, appetite depressant, obesity, nausea, pain, neuropathic pain, anxiety, Alzheimer's disease, amyotrophic lateral sclerosis (ALS), gastrointestinal aliments, hypertension, incontinence, pruritus, arthritis, arthrosis, rheumatic inflammation, Insomnia, mycosis, local or chronic pain, inflammation, attention deficit and hyperactivity disorder (ADDH), vomiting, atopic dermatitis, fibromyalgia, AIDS patients, mood disorders, erectile dysfunction, Premature ejaculation, nutritional deficiency, autism, spasticity, IBD, Crohn's disease, diabetes and bone growth stimulation, autism, spasms, spasmatic neurological patients.

In some specific embodiments, the compositions described herein are for use in treating pain.

It is further conceived that therapeutic methods using the cannabinoids of the invention may be part of combination therapies comprising administering to the mammal at least one additional therapeutic agent.

It is another aspect of the present invention to provide a composition for oral administration for use for treating or ameliorating the symptoms of at least one disorder or a disease in a mammal, the composition comprising an effective amount of at least one lipophilic active substance and at least one phospholipid, in the absence of fat glycerides.

Still further, it is contemplated that for the purpose of some of the embodiments the compositions of the invention may further comprise at least one additional therapeutic agent selected from group of an antibiotic, an anti-inflammatory, an analgesic, an antipsychotic agent, and a vitamin, antidiabetic, hypoglycemic agent, metformin, an omega supplement or a mineral nutrient.

Therefore, it is further contemplated that for the purpose of some embodiments the above methods may further comprise oral administration to the mammal at least one additional therapeutic agent. The administration may be 'concomitant administering' or 'co-administering', meaning administration of any type of therapeutic, bioactive agent and state-of-the-art medicament, together within a certain time period with the compositions of the invention. The time period is preferably less than 72 hours, such as 48 hours, for example less than 24 hours, such as less than 12 hours, for example less than 6 hours, such as less than 3 hours. These terms may also mean that the compositions of the invention and the additional therapeutic agent are administered together. While the compositions of the invention are administered orally, when administered in combination with an additional therapeutic agent, the agent may be administered orally or by any other administration route known in the art.

Further in this connection, therapeutic drug doses in the form of a composition of the invention can be further adapted to individual preferences and dosing regimens. For example, the drug/phospholipid composition of the invention can be shaped and coated as pellets, drops, candies, sugar coated, film coated, gelatin coated, Eudragit coated, or produced as a molded compressed matrix, swelling matrix, polysaccharide-based soft gel shells, or encapsulated in different types of capsules, in hard gelatin or soft gel capsules, cellulose capsules, etc., according to individual presences and needs. Further, the therapeutically effective amount can be easily adapted, increased or decreased to maximize the likelihood of therapeutic efficacy and to minimize the risk of drug toxicity, which in essence is personalized medicine. One of the common methods is by 'trial and error' starting from a minimal or a standard dose.

In further embodiments, the composition of the invention constitutes a semisolid composition for oral administration, the composition comprising at least one cannabinoid and at least one phospholipid, in the absence of fat glycerides, the composition providing an immediate and prolonged therapeutic effect.

It is further conceived that for the purpose of stability of the active components, as well as taste, smell, compositions according to the invention may further comprise certain quantities and proportions of at least one additive selected from an antioxidant, a surfactant, a viscosity increasing agent, a hardener, a viscosity decreasing agent, a color- and a flavor-imparting agent, or a salt, or any combination thereof.

Various sweeteners, taste modifiers, antioxidants, preservatives which are well known in the art may serve these purposes. For example, taste modifiers such as menthol, artificial sweeteners, plant sweeteners, plant extracts, plant juice, orange juice, passion fruit juice, lemon juice, sugars, honey, citrate, acids, menthol; antioxidants such as vitamins E (tocopherol, tocopheryl derivatives), vitamin C and derivatives, butylated hydroxyanisole (BHA), butylated hydroxytolune (BHT) recognized as GRAS, and sulfides and bisulphides, 5SA, any sweetener allowed for oral administration such as sugar, glucose, cyclamate, sucrose, saccharin, fructose, maltose, stevia extract, sodium saccharine; salts such as NaCl, $NaHCO_3$, $Na_2CO_3$, citrate, and others.

It is further contemplated that compositions of the invention may contain other additives such as: antioxidants; starch, flour, corn flour, polysaccharides, tapioca and similar; surfactants approved for oral use, such as cremophors and further various emulsifying agents; waxes such as beeswax, paraffin wax, plant wax; and various solidifiers and viscosity modifiers such as stearic acid, cetyl acid, polymers, cetyl alcohol, cetostearyl alcohols, stearyl alcohol; and specific viscosity enhancers such as alginate, PG alginate, Carbopol, mucoadhesive polymers, Carbophils, celluloses, Pluronics and Pluronic F127.

In some embodiments, compositions according to the invention may be selected to comprise any of the following combinations according to the invention:

Cannabidiol (CBD)+Phospholipon 90H,
Cannabidiol (CBD)+Phospholipon 90G,
CBD+THC+phospholipid,
CBD+THC+Phospholipon 90 G,
CBD+THC+Phospholipon 90 G+terpene,
Cannabinoid+phospholipid,
Cannabinoid+soy phospholipid,
Cannabinoid+lecithin,
CBD+Phospholipon 90 G,
Cannabinoid+Phospholipon 80 H+Vitamin E,
Cannabinoid+Phospholipon 80 H+Vitamin E+Menthol,
Cannabinoid+Phospholipon 90 H+Menthol,
CBD+Phospholipon 80 H+Vitamin E+Menthol,
THC+CBD+Phospholipon 90 H+Vitamin E+Menthol,
THC+phospholipid,
THC+Phospholipon 90G,
Cannabinoid+phospholipid+terpene,
Cannabidiol+phospholipid,
Cannabidiol+phospholipid, THC+phospholipid,
Cannabidiol+THC+lecithin,
Cannabidiol+phospholipid+menthol,
Cannabidiol+THC+menthol,
Cannabidiol+THC+phospholipid+menthol,
*Cannabis* extract+phospholipid,
CBD+Lipoid S100,
CBN+THC+Lipoid SPC,
Phospholipon 90 G+Phospholipon 90H+Cannabinoid,
CBN+lecithin,
CBN+phospholipid containing >60% phosphatidyl choline,
CBN+melatonin+phospholipon
CBN+melatonin+lipoid
Phospholipid+vitamins.

It is yet another aspect of the invention to provide a kit for preparing at least one lipophilic active substance for oral administration, and providing a prolonged therapeutic effect, the kit comprising (a) at least one lipophilic active substance, in a first unit dosage form, (b) at least one phospholipid, in a second unit dosage form; and optionally (c) a container for mixing (a) and (b), the kit being free of fat glycerides.

In some embodiments, the kit may further comprise additional therapeutic agent(s) that is specific to a clinical disease or disorder. In such case, the kit may be applicable to a specific clinical condition.

It should be appreciated that in other embodiments, the therapeutic agent(s) may be any agent suitable for ameliorating the treated disease.

More specifically, the kit may include means for containing separate constituents (a) and (b); such as a divided bottle or a divided foil packet, the separate compositions may also be contained within a single, undivided container. Typically the kit includes directions for preparing a specific mixture of constituents (a) and (b) according to the previously described proportions. The kit form is particularly advantageous as the specific formulation according to the invention can be prepared ad hoc at the room temperature. It should be appreciated that the kit of the invention is intended for achieving a controlled and individualized therapeutic effect. Further, the end-product of such kit can be molded and formed according to personal preferences and needs. Still further, the kit may comprise favoring agents and other additives according to personal use.

In some embodiments, the kit may comprise as a constituent (a) at least one cannabinoid.

Also provided is a drug delivery system for providing immediate and prolonged or prolonged effect of at least one lipophilic active substance for oral administration, the drug delivery system comprising at least one lipophilic therapeutically active substance and at least one phospholipid, in the absence of fat glycerides, and optionally further comprising at least one additive.

Specific Embodiments of the Invention

The following examples are representative of the new technology and techniques employed by the inventor in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

The following abbreviations are used in the examples below:

| Chemical | Abbreviation |
| --- | --- |
| Tetrahydrocannabidiol | THC |
| Cannabidiol | CBD |
| Phospholipon 90 G | PL 90G |
| Phospholipon 90H | PL 90H |

Example 1: Effect of Novel Cannabinoid Formulations in a Mice Model of Pain

Formulation and Preparation
Rx:
10 mg cannabidiol (CBD purchased from STI Pharmaceuticals, UK) and 90 mg Phospholipon 90G (PL 90 G, purchased from Lipoid GmbH, Germany) were mixed thoroughly in a mortar with pestle for 5 minutes to obtain a compact viscous mass. The mass was left overnight. The translucent mass was divided and shaped in small dosage forms suitable for oral administration to mice. The dosage forms were administrated per os at a drug dose of 50 mg/kg, corresponding to 1 mg CBD in 10 mg mass per animal to model mice tested in an acetic-acid writhing test.

Animal Studies

This experiment was performed on 24 female C57Bl/6J mice (8-9 weeks). Animals were housed under standard conditions of light and temperature in plastic cages. Animals were provided with unlimited access to water and food, with being individually inserted in separated cages with smooth flat floor.

The analgesic effect of the CBD-phospholipid formulations were tested at five time points, 1, 3, 6, 8 and 10 hours after oral administration of the CBD-phospholipid formulation. At the indicated time points, mice were anesthetized by isoflurane up to one minute, and then immediately intraperitoneal (IP) injected with (10 ml/kg) of 0.6% v/v acetic acid solution.

The number of writhing episodes was recorded by counting the number of writhes 5 minutes after acetic acid administration for a period of 10 minutes. Writhes were indicated by the abdominal constriction and stretching of at least one hind limb. The analgesic effect of the CBD phospholipid formulation was evaluated in terms of mean number of writhing episodes (Table 1), and further in terms of MPE (Maximum Possible Effect) values (Table 2). MPE % was calculated using the following equation: [Mean of writhing in control group−number of writhing in each mouse in treated group]/[Mean of writhing in control group]×100.

Treatments and Writhing Test

Twenty four mice were divided into six groups of four animals for various time treatments. Groups 1 to 5 were treated orally with the CBD at a drug dose of 50 mg/kg, being 1 mg CBD in 10 mg dosage per animal.

In Group 1, the mice were injected with acetic acid 1 hour after oral treatment with pellet comprising a formulation of the invention; Group 2-3 hours after oral treatment with pellet comprising a formulation of the invention; Group 3-6 hours after oral treatment with pellet comprising a formulation of the invention; Group 4-8 hours after oral treatment with PL pellet comprising a formulation of the invention; and Group 5-10 hours after oral treatment with pellet comprising a formulation of the invention. Group 6 included mice anesthetized by isoflurane without treatment, that served as untreated control.

Results and Conclusions

The results of the above experiment are presented in Tables 1 and 2, and FIG. 1, which is a graphic representation of the results provided in Table 1.

TABLE 1

Mean number of writhing episodes at 1, 3, 6, 8 and 10 hours in treated versus untreated control groups (Mean ± SD).

| | Time points (hours) | | | | | Untreated control |
|---|---|---|---|---|---|---|
| | 1 | 3 | 6 | 8 | 10 | |
| Writhes Count | 16.5 ± 4.8 | 15.7 ± 4.0 | 13.3 ± 1.7 | 13.0 ± 2.6 | 13.8 ± 3.9 | 30.3 ± 2.1 |

$p < 0.05$ for all treatment times vs. untreated control.

TABLE 2

MPE % values at 1, 3, 6, 8 and 10 hours.

| | Time points (hours) | | | | |
|---|---|---|---|---|---|
| | 1 | 3 | 6 | 8 | 10 |
| MPE % | 45.5 | 42.6 | 56.2 | 57.0 | 54.5 |

The results of Table 1 and Table 2 and FIG. 1 showed that administration of oral compositions of CBD dosage as described herein led to a rapid pronounced analgesic effect, maintained as a plateau for at least 10 hours (last point measured). More specifically, drug activity showed plateau effect starting from the first hour until the last time point measured. Thus, the formulation administrated orally to the pain animal model allowed for efficient immediate and very prolonged action of the drug.

Example 2: Exemplary Formulations According to the Invention

The present inventive concept provided a platform formulation for various lipophilic drugs. Below is an exemplary list of novel compositions according to some embodiments of the present invention:

Cannabinoid compositions comprising phospholipids, hydrogenated phospholipids, ceramides and/or phospholipid mixtures;

Cannabinoid compositions comprising CBD extract from *Cannabis sativa*, *Cannabis indica*, and their various species, and/or mixture of natural or synthetic cannabinoids in various w/w proportions:

THC 10 mcg+CBD 50 mg+Lecithin 90 mg,
THC 50 mcg+Phospholipid 90 mg,
THC 250 mcg+CBD 50 mcg+Lecithin 150 mg,
CBD 100 mcg+Soy phosphatidyl choline 50 mg,
THC 10 mcg+CBD 50 mcg+Phospholipon 90 G 100 mg,
THC 50 mcg+CBD 50 mcg+Phospholipon 90 G 100 mg,
Cannabinoid 200 mcg+Vitamin E 5 mg+Phospholipid 100 mg,
Cannabinoid 200 mcg+alpha tocopherol 5 mg+Phospholipid 100 mg,
Cannabinoids 50 mcg+Phospholipid 100 mg,
CBD 200 mg+Phospholipon 150 mg+50 mg Menthol,
CBD 100 mg+Phospholipon 90 H 150 mg+50 mg Menthol+5 mg alpha tocopherol,
CBD 0.01-1: Phospholipon 90G 99.99-0.5,
THC 0.01-1: Phospholipon 90G 99.99-0.5,
CBD 0.01-1: Phospholipon 90H (hydrogenated) 99.99-0.5,
CBD 0.01-1: Lecithin 99.99-0.5,
CBD 0.01-1: Soy lecithin 90G 99.99-0.5,
CBD 0.01-1: Hydrogenated Soy lecithin 99.99-0.5,
CBD 0.01-1: Egg lecithin 99.99-0.5,
THC 0.01-1: Phospholipon/Hydrogenated Phospholipon 9 99.99-0.5,
THC 0.01-1: Lecithin/Hydrogenated Lecithin 99.99-0.5,
CBD+THC 0.01-1: Lecithin/Hydrogenated Lecithin 99.99-0.5,
CBD+THC 0.01-1: Phospholipid 99.99-0.5,
CBD+THC 0.01-1: Phospholipon/Hydrogenated Phospholipon 99.99-0.5,
CBD+THC 0.01-1: Lecithin/Hydrogenated Lecithin 99.99-0.5+antioxidant,
CBD+THC 0.01-1: Phospholipid 99.99-0.5+antioxidant,
CBD+THC 0.01-1: Phospholipon/Hydrogenated Phospholipon 99.99-0.5+antioxidant,
CBD+0.01-1: Lipoid S100 99-0.5+antioxidant,
CBD+Lipoid S 0.01-1: Lipoid S100 99-0.5+antioxidant,
Cannabinoid 0.01-1: Lipoid S100 99-0.5+antioxidant,
Cannabinoid 0.01-1: Lipoid S 99-0.5+antioxidant.

Example 3: Exemplary Formulations According to the Invention

The present inventive concept further provides a platform formulation for various cannabinoid compositions comprising various cannabinoid(s) and phospholipid(s) amounts, as indicated below:

Cannabinoid/s 1, 5, 10, 20, 50 mg–Phospholipids 10-300 mg,
Cannabinoid/s 1, 5, 10, 20, 50,100 mg–Phospholipids 10-700 mg,
Cannabinoid/s 1, 5, 10, 20, 50,100 mg–Phospholipon 10-700 mg,
Cannabinoid/s 1, 5, 10, 20, 50 mg–Lecithin 10-700 mg,
Cannabinoid/s 1, 5, 10, 20, 50 mg–Soy Lecithin 10-700 mg,
Cannabinoid/s 50, 100, 200, 500, 1000 mcg–Phospholipids 10-500 mg,
Cannabinoid/s 50, 100, 200, 500, 1000 mcg–Lecithin 10-500 mg,
Cannabinoid/s 50, 100, 200, 500, 1000 mcg–Soy Lecithin 10-500 mg,
Cannabinoid/s 50, 100, 200, 500, 1000 mcg–Phospholipon 90 10-500 mg,
Cannabinoids 50 mg–Lecithin 50 mg,
Cannabinoids 100 mg–Phospholipon 50 mg,
THC 10 mg+Phospholipid 200 mg,
THC 9 mg+CBD 1 mg+Phospholipid 250 mg,
THC 9 mg+CBD 1 mg+Lecithin 250 mg,
THC 9 mg+CBD 1 mg+Phospholipon 90 250 mg,
THC 9.5 mg+CBD 500 mcg+Phospholipid 250 mg,
THC 20 mcg+Phospholipid 250 mg,
THC 50 mg+Phospholipid 350 mg,
CBD 20 mg+THC 20 mg+Phospholipid 400 mg,
CBD 300 mg+Lipoid S100 700 mg,
CBD 100 mg+Lipoid S 850 mg+Vit E 50 mg,
CBD 90 mg+Lipoid S 850 mg+Vit E 50 mg+BHT 10 mg,
CBD 200 mg+Phospholipon G+Phospholipon H+Vit E.

Any one of the formulations described herein may comprise at least one additional agent such as analgesics, antacids, antianxiety drugs, anti-arrhythmics, anti-bacterials, antibiotics, antimicotics, anticoagulants and thrombolytics, anticonvulsants, antidepressants, antidiarrheals, antiemetics, antifungals, antihistamines, anti-hypertensives, anti-inflammatories, antineoplastics, antipsychotics, antipyretics, antivirals, barbiturates, beta-blockers, bronchodilators, cold cures, cholesterol lowering drugs, corticosteroids, cough suppressants, cytotoxics, decongestants, diuretics, expectorant, hormones, hypoglycemics, immune-suppressives, laxatives, muscle relaxants, sedatives, sex hormones, sleeping drugs, tranquilizer and vitamin supplements, such as omega fatty acids, omega-3-fatty acids, EPA, DHA, ALA.

Example 4: Exemplary Formulations According to the Invention

The present inventive concept further provides a platform formulation for various compositions comprising cannabinoids and/or other lipophilic drugs or therapeutically active substances, as listed below:
Rotigotine 25 mg+Lecithin 225 mg,
Vitamin D 10 mg+Phospholipon 90 G 90 mg,
CBD 50 mg+Lipoid S 100 700 mg,
CBD 50 mg+Lipoid S 100 500 mg+Phospolipon 90 H 30 mg,
CBN 2.5 mg+Melatonin 5 mg+Phospholipon 90 G: Phospholipon 90 H (3+1) 100 mg,
CBN 5 mg+CBD 2 mg+Phospholipon 90 G 100 mg,
THC 1 mg+CBD 300 mg+Lipoid S100700 mg,
5SA 250 mg+Soy Lecithin 600 mg,
Plant extract+Phospholipon 90 G 1:9,
Fruit extracted juice+Phospholipid 1:9,
Citrus juice 50 mg+Phospholipon 80 G 450 mg,
Orange juice 70 mg+Lipoid S 100 630 mg,
Ginger extract+Phospholipon 90 G,
CBD 20 mg+Plant extract 30 mg+Phospholipon 90 G 250 mg.

Example 5: Cannabinoid Dosage Form Preparation Method

A mixture of cannabinoids and phospholipids is thoroughly mixed for 10-30 minutes in a mixer, mortar, mortar type mixer, malaxation mixer or any apparatus able to thoroughly mix the components. A mass is formed. The mass is left for 1-24 hours, when generally the mass becomes more translucent. The mass is then cut, shaped, molded, or optionally rolled with roller, cut and shaped. The shapes are of any adequate form oral administration, such as bean, jellybean, ball, sphere, knob, pellet, with a weight from a few mg to hundreds of mgs. The forms are optionally coated with sugar, glazer, films, polymers, acrylates, polyacrylates, Eudragits, celluloses, cellulose derivatives, chitosans, gelatin, wax, any coating for oral administration, extruded and encapsulated in hard gelatin capsules or polymer capsules. It should be appreciated that the mixing time depends on the quantities and components.

The capsules are optionally coated with functionality films or inert films. In some cases functional films may be used, e.g., for achieving specific pH disintegration. The films may be composed of polymers such as acrylates, polyacrylates, Eudragits, celluloses, cellulose derivatives and chitosans.

Example 6: Cannabinoid Dosage Form

A composition comprising: a lipophilic drug 0.01-10: phospholipid 70-90:Vitamin E 0.5-2 was prepared and packaged in a hard gelatin capsule.

Example 7: Disintegration Test for the Dosage Forms Comprising Cannabinoids

To test the disintegration behavior of the innovative dosage forms for oral delivery of cannabinoids, the following compositions were prepared:
PL Carrier and CBD at a PL carrier to CBD ratio of 6:4,
PL Carrier and CBD at a PL carrier to CBD ratio of 7:3, and
PL Carrier and THC at a PL carrier to THC ratio of 9:1.
In all compositions, the phospholipid Carrier (PL Carrier) comprised PL 90H and PL 90G at a PL 90H to PL 90G ratio of 9:1.

In each composition, the components were mixed at room temperature to obtain a compact mass. The mass was left overnight. Then, the drug containing mass was rolled by hands in round balls or elongated forms. The dosage forms were shacked in 200 ml simulated gastric fluid for 2 h, then transferred to other flasks containing 200 ml simulated intestinal fluid and the integrity observed for 24 h, during which the flasks were shaken. The incubation temperature was 37° C. in the two incubation steps.

The simulated gastric fluid included 0.5% v/v HCl solution, pH=1-2, followed by simulated intestinal fluid that included 0.68% w/v $KH_2PO_4$, 0.089% w/v NaOH, pH=6-7.
Results and Observations The mass maintenance behavior of the above compositions is presented in FIGS. 2-4. FIGS. 2A to 2L and FIGS. 3A to 3L show that the CBD dosage form mass remained non disintegrated during the incubation period of 24 hours in the gastric and intestinal fluids. As seen in FIGS. 4A to 4L, for the formulation containing THC, the mass remained non disintegrated but porous at 1 hour incubation in gastric fluid (FIG. 4C). By the end of the experiment following incubation in intestinal medium, the volume of the THC dosage form was increased by approximately two and half folds. Some floating was observed at certain time points with the THC and with the low CBD concentration dosage forms. All tested formulations did not disintegrated during the test time in both, gastric and intestinal, media.

Example 8: Disintegration Experiment of a Mass Containing Sudan III

Preparation Method
PL and Sudan III (a lysochrome fat-soluble diazo dye) were mixed mechanically. A red mass was obtained. Sudan III formulations appearance following incubation in simulated gastric and intestinal fluids at 37° C. with shaking for 48 hours.
Results FIG. 5A to 5F show images of the formed mass at different incubation times after incubation in simulated gastric fluid at 37° C. for 4 h followed by incubation in intestinal fluid at 37° C. for an additional 48 h. FIGS. 5A to 5C are images of a mass formed from Sudan III:PL at a ratio of 0.1:9.9, incubated 4 h (FIG. 5B) and 48 h (FIG. 5C) with FIG. 5A being control. FIGS. 5D to 5F are images of a mass formed from Sudan III:PL at a ratio of 1:9, incubated 4 h (FIG. 5E) and 48 h (FIG. 5F) with FIG. 5D being control.

The results indicate that the mass did not disintegrate during the incubation in the gastric acid and in the intestinal medium. A slight erosion of the mass was observed at the end of the 48 hours, showing a small cloud layer around the non-disintegrated mass.

Conclusion

The results indicate that the mass remained non-disintegrated with some erosion at the end of 48 hours experiment.

Example 9: Effect of a Composition of a Composition Comprising THC and CBD Administered Orally Vs Control Composition—a 10 Hours Test Twenty five mg compositions containing the drugs were administrated orally to mice, each mice receiving 2.5 mg (100 mg/kg) CBD and 0.025 mg (1 mg/kg) THC. Using these amounts of CBD and THC, two preparations were made: one dosage form according with the present disclosure comprising CBD:THC:PL90G at a ratio of 10:0.1:89.9 and a control oral formulation containing CBD:THC: (ETOH+PG) at a ratio of 10:0.1:89.9.

Experimental Protocol

Animals

This experiment was performed on CD-1 ICR mice (21-25 g). Mice were housed under standard conditions of light and temperature in plastic cages in the specific-pathogen unit (SPF) of the pharmacy school at the Hebrew University Animals were provided with unlimited access to water and food, with being individually inserted in separated cages with smooth flat floor.

Treatments and Writhing Test

The test was carried out on two treatment animal groups, one group with the formulation of the invention and one group with the control formulation, and one untreated group (animals anesthetized with Isoflurane® injected with acetic acid at the same dose without treatment served as untreated control).

The number of writhing episodes was recorded by counting the number of writhes 5 minutes after acetic acid administration for a period of 20 minutes. Writhes were indicated by the abdominal constriction and stretching of at least one hind limb.

The analgesic effect of each treatment is expressed by the Maximum Possible Effect (MPE %) of the treatments, which is directly related to the efficiency of the treatment, and is calculated according to the following equation:

Results

The results of this experiment show the prolonged antinoceceptive effect of the cannabinoids administered in the new oral formulations as compared to the control oral preparation.

TABLE 3

MPE % values in mice treated with 2.5 mg (100 mg/kg) CBD and 0.025 mg (1 mg/kg) THC per os from the new oral composition as compared to control 10 hours prior to IP injection of acetic acid and compared to untreated control mice

| Treatment | MPE % at 10 h following treatment |
| --- | --- |
| New oral formulation | 60.1 |
| Control oral solution | 15.2 |

The results indicate that administration of CBD-THC novel formulation had excellent antinoceceptive effect even 10 hours after administration having an MPE % value of 60.1%. On the other hand, the administration of oral solution (control) lead at the same time point of 10 h, to a much lower effect of only 15.2% MPE for the control formulation.

The new finding of the antinociceptive efficiency of a combination of a very low concentration/dose of the THC versus a high concentration/dose of CBD (100 times) This may be very significant in new treatments in which the dose of THC (responsible for "high"), could be drastically reduced or even eliminated from treatments.

Example 10: Disintegration Behavior of a Composition Packaged in Hard Gelatin Capsules Versus a Capsule Containing a Control Composition To test the disintegration behavior of a composition of the invention encapsulated in a hard capsule in comparison with a capsule with a control formulation, the capsules were incubated in simulated gastric fluid for 2 h then in simulated intestinal fluid for additional 8 hours.

The following formulations were tested:

Composition A (100 mg): CBD 10% w/w and PL 90G 90% w/w were mixed for translucent mass formation and then encapsulated in a transparent hard gelation capsule.

Composition B—control (100 mg): CBD 10% w/w mixed with 40% w/w PL 90G and with 50% w/w Olive Oil. The mixture was then encapsulated in a transparent hard gelatin capsule.

Both formulations were tested as follows: simulated gastric fluid (0.5% v/v HCl solution, pH=1-2), simulated intestinal fluid (0.68% w/v $KH_2PO_4$, 0.089% w/v NaOH, pH=6-7). The capsules were shacked at 37° C. in 200 ml simulated gastric fluid for 2 h, and transferred to other flasks containing 200 ml simulated intestinal fluid for additional time. The appearance of the capsules was registered and photographed at different time points.

Results and Observations

Figure 6B:
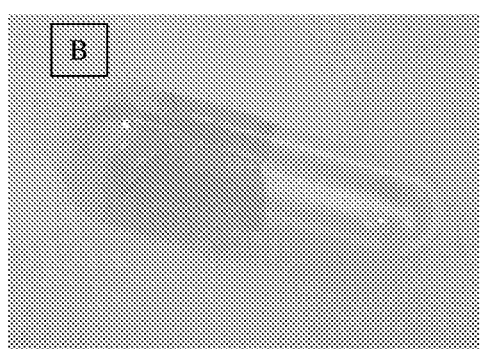
Figure 7A:
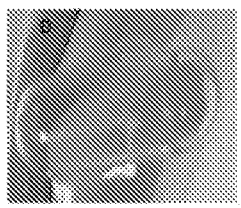
FIGS. 7A-7D provide images showing the behavior of capsule containing formulation according with the present disclosure at different time points after incubation.
Figure 7B:
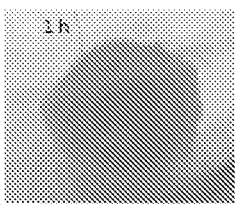
Figure 7C:
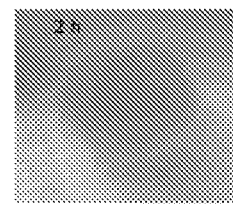
Figure 7D:
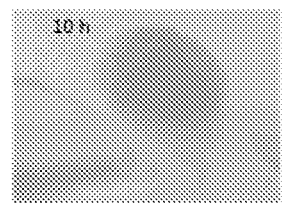
Figures 8A, 8B, 8C, 8D:
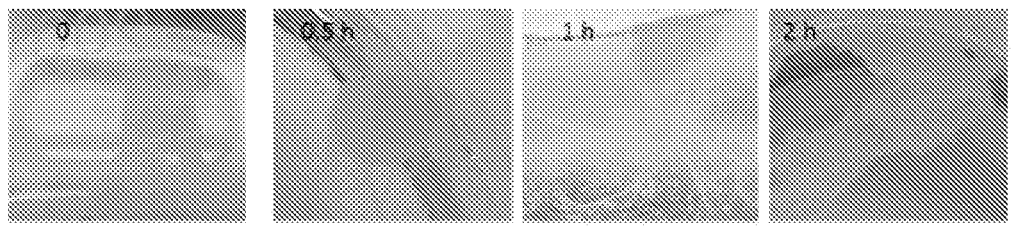
FIG. 8A—before incubation, FIG. 8B—0.5 h after incubation in simulated gastric fluid, FIG. 8C—1 h after incubation in simulated gastric fluid, and FIG. 8D—2 h after incubation in simulated gastric fluid at 37° C.

The behavior of the capsules containing formulation A and the comparator (formulation B) is presented in FIGS. 6 to 8. As it can be seen in FIGS. 7B and 8B, the wall of the capsules dissolved in the first 30 min in gastric acid for the two formulations. However, as shown in FIGS. 7C and 7D, the formulations according with the present disclosure behaved differently. Namely, the mass of the composition according the present disclosure, remained non-disintegrated in the gastric and intestinal fluid until the end of the incubation period. It should be noted that a very slight and slow erosion was observed on the surface of the mass of the present disclosure staring from 30 min of incubation.

On the other hand, in the control formulation a rapid disintegration started in the early stages. As seen in FIG. 8D after 2 h incubation in the gastric fluid, the control formulation completely disintegrated, oily drops were observed on the surface of the incubation medium. This formulation was too liquid to be transferred to the intestinal fluid, being fully disintegrated.

Example 11: Immediate and Prolonged Antinociceptive Effect in an Animal Model of THC Oral Dosage Form To evaluate the prolonged antinoceceptive effect of THC administered orally from a new formulation in animal pain mice model as compared to untreated animals, the following experiments were carried out.

Materials and Methods

Materials

PL 90G, THC, VITAMIN E, Glacial Acetic Acid

Dosage Form Composition and Preparation

The mass was prepared from 5% THC and 95% carrier (composed of PL 90G:Vit E, 9.5:0.5). THC was mixed well with the carrier by mechanical mixing.

Experimental Protocol

Animals

This experiment was performed on female C57Bl/6J mice (8-9 weeks). Mice were housed under standard conditions of light and temperature in plastic cages in the specific-pathogen unit (SPF) of the Pharmacy School at the Hebrew University Animals had unlimited access to water and food, with being individually inserted in separated cages with smooth flat floor.

Treatments and Writhing Test

Mice were divided randomly into 7 groups—6 treatment groups and one group of untreated animals. Animals were treated orally with a 5% THC formulation at a dose of 10 mg/kg 1, 3, 6, 8, 10 or 12 hours before pain induction The mean THC dose per mouse (mouse weighing ~20 g) was 0.2 mg administered in a 4 mg dosage form. At predetermined time points after treatment, the mice were anesthetized by Isoflurane® up to one minute, then immediately injected with (10 ml/kg) of intraperitoneal (IP) 0.6% v/v acetic acid solution.

The seventh animal group (n=5) served as control untreated animals. Animals in this group were anesthetized with Isoflurane® injected with acetic acid at the same dose without treatment.

The number of writhing episodes was recorded by counting the number of writhes 5 minutes after acetic acid administration for a period of 10 minutes. Writhes were indicated by the abdominal constriction and stretching of at least one hind limb.

The analgesic effect of the THC is expressed by the Maximum Possible Effect (MPE %) of the treatments, which is directly related to the efficiency of the treatment, and is calculated according to the following equation: [Mean of writhing in control group−number of writhing in each mouse in treated group]/[Mean of writhing in control group]*100.

Results

Figure 9:
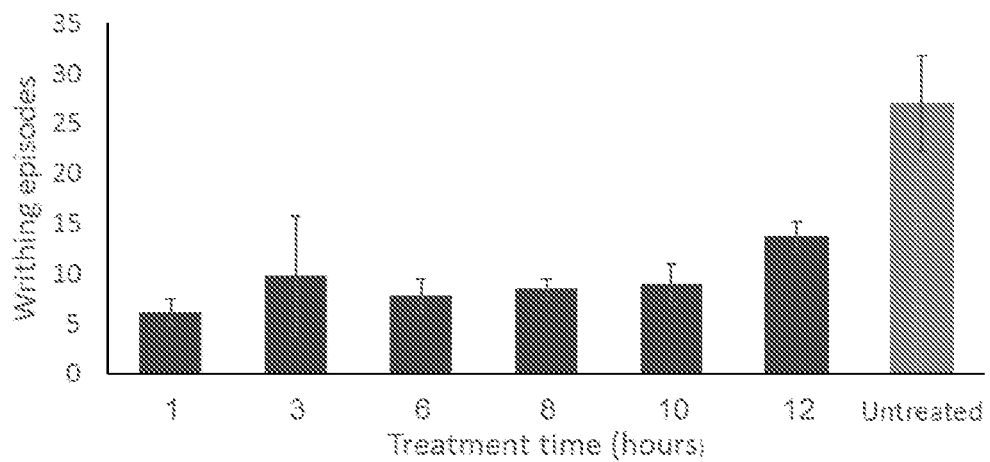
FIG. 9 provides a bar representation of the mean writing counts in mice treated with 10 mg/kg THC per os from a an oral formulation according with some embodiment of the present disclosure 1, 6, 8, 10 and 12 hours prior to IP injection of acetic acid vs. untreated mice (Mean±SD). p<0.05.

The results of this experiment testing the prolonged antinoceceptive effect of THC administered in the new oral formulation are presented in Tables 4, 5 and FIG. 9.

TABLE 4

Mean number of writhing episodes in mice treated with 10 mg/kg THC per os from new oral formulation 1, 3, 6, 8, 10 and 12 hours prior to IP injection of acetic acid as compared to untreated control mice group (Mean ± SD)

| | Time point (hours) | | | | | | Untreated Control |
|---|---|---|---|---|---|---|---|
| | 1 | 3 | 6 | 8 | 10 | 12 | |
| Writhes Count | 6.2 ± 1.3 | 9.8 ± 5.9 | 7.8 ± 1.6 | 8.5 ± 1.0 | 9.0 ± 2.0 | 13.7 ± 1.5 | 27.0 ± 4.8 |

TABLE 5

Mean MPE % values in mice group treated with 10 mg/kg THC per os from the new oral formulation 1, 3, 6, 8, 10 and 12 hours prior to IP injection of acetic acid

| Time point (hours) | 1 | 3 | 6 | 8 | 10 | 12 |
|---|---|---|---|---|---|---|
| MPE % | 77.0 | 63.7 | 71.1 | 66.7 | 69.6 | 49.4 |

The results show that the THC novel oral dosage form administrated to pain model animal lead to a rapid analgesic effect starting from 1 hour (77.0% MPE). The effect was prolonged showing a plateau effect for more than 10 hours following administration.

The invention claimed is:

1. A prolonged release oral pharmaceutical formulation in the form of a solid or semisolid compact mass, consisting of:
   at least one cannabinoid;
   at least one phospholipid, said at least one cannabinoid being solubilized in said at least one phospholipid; and
   optionally, at least one additive selected from the group consisting of an antioxidant, a surfactant, a taste masking agent, a color-imparting agent, a flavor-imparting agent, a viscosity increasing or viscosity decreasing agent, a salt, and any combination thereof,
   wherein said at least one phospholipid constitutes from 60-90 wt % of the formulation and the formulation is free of water and fat glycerides, and
   wherein said formulation is in the form of a solid or semisolid compact mass in unit dosage form, optionally encapsulated, from which, when administered orally, said cannabinoid diffuses for at least 10 hours so as to provide a prolonged therapeutic effect of at least 10 hours.

2. The formulation according to claim 1, wherein the at least one cannabinoid is an extract from the *cannabis* plant species Avidekel.

3. The formulation according to claim 1, wherein the formulation further consists of at least one additive selected from the group consisting of an antioxidant, a surfactant, a taste masking agent, a color-imparting agent, a flavor-imparting agent, a viscosity increasing or viscosity decreasing agent, a salt, and any combination thereof.

4. The formulation according to claim 1, being in the form of individual doses for oral administration, wherein an effective amount of said at least one cannabinoid is present in each dose.

5. The formulation according to claim 1, wherein the at least one cannabinoid is selected from the group consisting of endocannabinoid, phytocannabinoid and synthetic cannabinoids.

6. The formulation according to claim 1, wherein the at least one cannabinoid is a dried whole extract of cannabinoid.

7. The formulation according to claim 1, wherein the at least one cannabinoid is selected from the group consisting of tetrahydrocannabinol (THC), cannabidiol (CBD), cannabinol (CBN), cannabigerol (CBG), cannabichromene (CBC), cannabivarin (CBV), cannabielsoin (CBE), cannabicyclol (CBL), tetrahydrocannabivarin (THCV), cannabichromevarin (CBDV), cannabichromevarin (CBCV), cannabigerovarin (CBGV), cannabigerol monomethyl ether (CBGM), iso-tetrahydrocannabinol (iso-THC) and any combination thereof.

8. The formulation according to claim 1, wherein the at least one phospholipid is glycerophospholipid or phosphosphingolipid.

9. The formulation according to claim 8, wherein the at least one phospholipid is selected from the group consisting of phosphatidylcholine (PC), phosphatidylinositol (Pl), phosphatidylserine (PS), phosphatidylethanolamine (PE), phosphatidic acid (PA), phosphatidylglycerol (PG) cardiolipin (CL) and any combination thereof.

10. The formulation according to claim 1, in extruded form.

11. The formulation according to claim 1, wherein the unit dosage forms are encapsulated in a soft gelatin capsule, a hard gelatin capsule or a polymeric capsule.

12. A prolonged effect pharmaceutical formulation in the form of a solid or semisolid compact mass, consisting of:
  at least one cannabinoid;
  at least one phospholipid, wherein said cannabinoid is solubilized in said phospholipid; and
  an additive selected from the group consisting of an antioxidant, a surfactant, a taste masking agent, a color- or a flavor-imparting agent, a viscosity increasing or viscosity decreasing agent, and a salt,
  wherein said at least one phospholipid constitutes from 60-90 wt % of the formulation, and the formulation is free of water and fat glycerides, and
  wherein said formulation is in the form of a solid or semisolid compact mass in unit dosage form, optionally encapsulated, from which, when administered orally, said cannabinoid diffuses for at least 10 hours so as to provide a prolonged therapeutic effect of at least 10 hours.

13. A prolonged release oral pharmaceutical formulation in the form of a solid or semisolid compact mass, comprising:
  at least one cannabinoid; and
  at least one phospholipid, said at least one cannabinoid being solubilized in said at least one phospholipid,
  wherein said at least one phospholipid constitutes from 60-90 wt % of the formulation and the formulation is free of water and fat glycerides, and
  wherein said formulation is in the form of a solid or semisolid compact mass in unit dosage form, from which, when administered orally, said cannabinoid diffuses for at least 10 hours so as to provide a prolonged therapeutic effect of at least 10 hours.

14. The formulation according to claim 13, wherein said at least one cannabinoid comprises cannabidiol (CBD) alone or in combination with one or more additional cannabinoids.

15. The formulation according to claim 1, wherein the formulation is free of alginate.

16. The formulation according to claim 12, wherein the formulation is free of alginate.

17. The formulation according to claim 13, wherein the formulation is free of alginate.

18. A prolonged release oral pharmaceutical formulation in the form of a solid or semisolid compact mass, comprising at least one cannabinoid and at least one phospholipid and no more than 5% solvent, the formulation being free of water and fat glycerides, said at least one phospholipid comprising from 60-90 wt % of the formulation, said formulation being produced by the process comprising:
  thoroughly mixing said at least one cannabinoid, said phospholipid, and said solvent, if present, at a w/w ratio selected to produce a solid or semisolid compact mass that is free of water and fat glycerides; and
  shaping said compact viscous mass into solid or semisolid dosage form units from which, when orally administered, said cannabinoid diffuses for at least 10 hours so as to have a prolonged therapeutic effect of at least 10 hours.

19. The formulation according to claim 18, wherein said shaping comprises cutting, extruding or molding.

20. The formulation according to claim 18, further including the step of encapsulating the shaped viscous mass in a hard or soft gelatin or polymer capsules.

21. The formulation according to claim 13, wherein the unit dosage form is encapsulated in a hard or soft gelatin or polymer capsule.

22. The formulation according to claim 13, wherein said at least one cannabinoid comprises a synthetic cannabinoid.

23. The formulation according to claim 13, wherein said prolonged therapeutic effect is maintained as a plateau for at least 10 hours.

24. The formulation according to claim 13 wherein said formulation, when administered orally, remains not fully disintegrated for at least 10 hours.

* * * * *